United States Patent [19]
Ferber

[11] Patent Number: 5,713,874
[45] Date of Patent: Feb. 3, 1998

[54] CAMOUFLAGED INJECTION NEEDLE

[75] Inventor: Jack Richard Ferber, New York, N.Y.

[73] Assignee: Kind-R-Ject Company, LLC, New York, N.Y.

[21] Appl. No.: 510,052

[22] Filed: Aug. 1, 1995

[51] Int. Cl.$^6$ .................... A61M 5/00; A61M 5/178; A61M 35/00; A61M 31/00
[52] U.S. Cl. ............... 604/198; 604/1; 604/202; 604/204; 604/212; 604/158; 604/164; 604/51
[58] Field of Search ................ 604/1, 75, 132, 604/142, 181, 183, 185, 187, 192, 197, 198, 199, 201, 202, 204, 212, 215–217, 3, 195, 51, 52, 54, 49, 200, 205, 206; 128/898

[56] References Cited

U.S. PATENT DOCUMENTS

| | | | |
|---|---|---|---|
| 2,724,383 | 11/1955 | Lockhart | 604/212 |
| 2,724,384 | 11/1955 | Berthiot | 604/212 |
| 3,469,579 | 9/1969 | Hubert . | |
| 3,530,492 | 9/1970 | Ferber . | |
| 3,906,932 | 9/1975 | Ayers . | |
| 4,243,035 | 1/1981 | Barrett | 604/1 |
| 4,258,713 | 3/1981 | Wardlaw | 604/198 |
| 4,282,986 | 8/1981 | Ekenstam et al. | 604/212 |
| 4,392,859 | 7/1983 | Dent | 604/198 |
| 4,543,092 | 9/1985 | Mehler et al. | 604/164 |
| 4,808,170 | 2/1989 | Thornton et al. | 604/274 |
| 4,958,901 | 9/1990 | Coombs | 604/44 |
| 5,064,411 | 11/1991 | Gordon, III | 604/48 |
| 5,207,658 | 5/1993 | Rosen et al. | 604/272 |
| 5,267,974 | 12/1993 | Lambert | 604/216 |
| 5,328,483 | 7/1994 | Jacoby | 604/212 |
| 5,342,320 | 8/1994 | Cameron | 604/192 |
| 5,377,874 | 1/1995 | Brown | 604/3 |
| 5,484,426 | 1/1996 | Yoon | 604/1 |

FOREIGN PATENT DOCUMENTS

| | | |
|---|---|---|
| 486146 | 11/1953 | Italy . |
| 114006 | 2/1926 | Switzerland . |
| 90/07348 | 7/1990 | WIPO . |

*Primary Examiner*—Corrine M. McDermott
*Assistant Examiner*—Ronald K. Stright, Jr.
*Attorney, Agent, or Firm*—Meltzer, Lippe, Goldstein, Wolf & Schlissel, P.C.

[57] ABSTRACT

A camouflaged injection needle is disclosed including a shaft, a flexible ellipsoid tip at one end of the shaft and a sharp needle tip positioned within the flexible tip and axially aligned with the shaft. The sharp needle tip is capable of piercing through the flexible tip and into an outer human tissue when the flexible tip is positioned on the outer human tissue and the shaft is urged in the direction of the outer human tissue. The injection needle is camouflaged to resemble a cotton swab. This reduces pre-injection anxiety of the patient.

22 Claims, 3 Drawing Sheets

CAMOUFLAGED INJECTION NEEDLE

FIELD OF THE INVENTION

The present invention relates to medical devices. More particularly, the present invention relates to injection needles for injecting a fluid into human tissues.

BACKGROUND OF THE INVENTION

Many injection needles are known in the prior art. See for instance, U.S. Pat. Nos. 3,469,579, 3,530,492, 3,906,932, 4,543,092, 4,808,170, 4,958,901, 5,064,411, and 5,207,658, French Patent No. 1,225,009, Italian Patent No. 486,146, Swiss Patent No. 114,006 and International Patent Publication No. WO 90/07348. U.S. Pat. No. 3,530,492 proposes a novel injection needle 10 which is shown in FIG. 1. The needle has a sharp outer tubular needle tip 11 with a short shaft and a flange 12. The short outer tubular needle tip 11 is sufficiently sharp to pierce an outer or uppermost human tissue layer (such as a mucous membrane or epidermal tissue) when manually urged towards the outer tissue layer. The outer tubular needle tip 11 penetrates through the uppermost tissues to the more delicate lower layer tissues below until the flange 12 meets the outer tissue layer surface. At such a point, continued pressure in the direction of the outer tissue dislodges an inner needle tip 15 and allows the inner needle 15 to slide out of a hole at the end of the outer tubular needle tip 11. The inner needle tip 15 has a blunt end 21. The inner needle tip 15 penetrates through the more delicate lower tissues by bluntly dissecting the inner tissues. That is, the blunt needle tip 15 tends to separate and pass between tissues rather than to pierce through them. The needle of FIG. 1 enables the administration of injections to tissues well below the uppermost tissue layers while minimizing the damage to the lower layer tissues.

Most small children, and some older persons have a fear of injections. Typically, such fears are triggered as soon as the injection needle is brought into the field of view of the patient. Such fears are undesirable since they tend to increase the perception of pain inflicted by the injection and to unsettle the patient in general. It is therefore an object to overcome the disadvantages of the prior art.

SUMMARY OF THE INVENTION

This and other objects are achieved by the present invention which provides a "camouflaged" injection needle. That is, the injection needle according to an embodiment of the present invention is camouflaged to appear like a cotton swab such as a Q-TIP™ manufactured by the Johnson and Jonson™ company.

Illustratively, the camouflaged injection needle has a hollow shaft, an easily puncturable (i.e., flexible) ellipsoid tip attached to one end of the shaft and at least one needle tip positioned within the flexible ellipsoid tip and axially aligned with the shaft. The needle tip is sufficiently sharp to puncture through the flexible ellipsoid tip and into an outer human tissue (epidermis, mucous membrane, etc.) when the ellipsoid tip is positioned adjacent to the outer human tissue and the shaft is urged towards the outer human tissue.

Illustratively, the overall needle appears like a cotton swab. The patient thus does not discover the nature of the injection needle until after the needle is urged through the flexible ellipsoid tip and outer human tissue. Pre-injection anxiety is therefore reduced.

The camouflaged injection needle may also be provided with a squeeze bulb at an end opposite to the flexible ellipsoid tip which also appears like a swab tip of a cotton swab. By squeezing the squeeze bulb, a fluid contained therein may be communicated via the hollow shaft towards the needle tip and injected into the patient via one or more holes in the vicinity of the needle tip.

The flexible ellipsoid tip may be made of an absorbent material such as foam. Alternatively, the ellipsoid tip may have a textured surface with pores. Either tip may be dipped into a topical agent, e.g., an antiseptic fluid or paste. In another embodiment, the flexible ellipsoid tip is sealed, e.g., within a membrane. The topical agent may be pre-applied to such a flexible ellipsoid tip. (The membrane prevents the agent from evaporating or becoming contaminated.) The ellipsoid tip may therefore be used to apply an antiseptic or other topical fluid prior to administering the injection. In such a case, the injection needle not only appears like a cotton swab but also can function like a cotton swab.

The needle tip which pierces through the flexible ellipsoid tip and outer human tissue may be a tubular outer needle tip which contains an inner blunt dissection needle tip within its bore. In such a case, the hollow outer needle tip only punctures and penetrates through the flexible ellipsoid tip and outer human tissue. The inner blunt dissection needle tip penetrates through the more delicate tissue below the outer human tissue via blunt dissection.

In short, a camouflaged injection needle is provided which appears like a cotton swab. The camouflaged injection needle alleviates pre-injection anxieties of patients.

DETAILED DESCRIPTION OF THE INVENTION

Figure 2A:
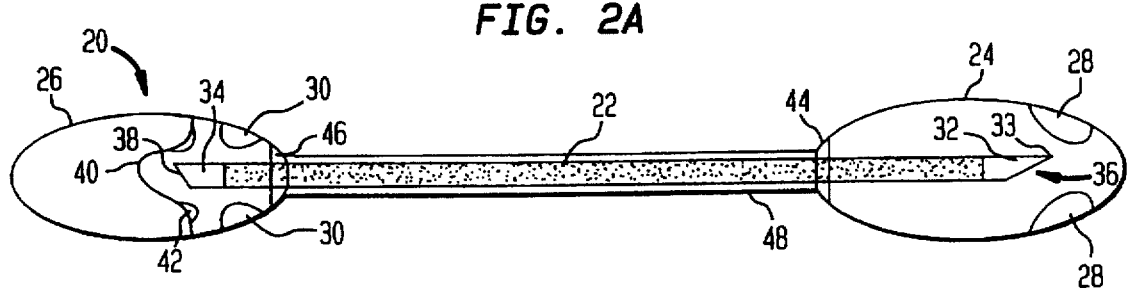
FIGS. 2(a)–(c) depict an injection needle according to a first embodiment of the present invention.

FIG. 2(a) depicts a camouflaged injection needle 20 according to an embodiment of the present invention. As shown, the camouflaged injection needle 20 has a shaft 22, which is illustratively hollow. The hollow shaft 22 may be made of metal or plastic or any other material commonly used for manufacturing injection needles. Illustratively, the hollow shaft may have a variety of dimensions, such as an outer diameter of about 10 to 30 gauge and a length of about 3" to 8". At one end of the shaft 22 is a flexible tip 24 which may be made out of an easily puncturable (i.e., flexible) material such as a urethane foam. The material used to make the flexible tip 24 may be absorbent or non-absorbent. In the case of a non-absorbent flexible tip 24, the flexible tip 24 may be formed with a textured surface that has pores. Illustratively, the texture of the flexible tip 24 is chosen so that a topical agent, i.e., fluid or paste readily adheres to the surface of the flexible tip 24.

At the opposite end of the shaft is a squeeze bulb 26 which may be made out of any opaque and resilient material that is also fluid tight such as rubber, plastic, etc. The squeeze bulb 26 may be graduated to indicate the volume of fluid therein. Illustratively, the axial length of the squeeze bulb 26 and flexible tip 24 may be in the range of 0.25" to 3". The squeeze bulb 26 and flexible tip 24 may also have a maximum thickness (perpendicular to the axis) of about 0.12" to 2". However, the squeeze bulb 26 and flexible tip 24 need not be the same size.

Illustratively, the squeeze bulb 26 contains a fluid therein such as a medicine or anesthetic fluid. The squeeze bulb may be designed to hold a specific volume of fluid. Illustratively, the volume of fluid is in the range of about 0.1 cc to 10 cc. Both the flexible tip 24 and squeeze bulb 26 are ellipsoid shaped (i.e., "bulbous") so as to resemble the swab tips of a cotton swab such as the Q-TIP™ cotton swab manufactured by the Johnson and Jonson™ company. (Herein, the term "cotton swab" is used to refer to all hygienic instruments comprising a shaft and one or more swab tips which may be made out of cotton, urethane foam or some other absorbent or non-absorbent material.) To distinguish the flexible tip 24 from the squeeze bulb 26, indicia, such as colored dots 28 and 30, may be provided on the outer surfaces of the flexible tip 24, the squeeze bulb 26, or both. Alternatively, the flexible tip 24 and squeeze bulb 26 may be differently shaped or colored. The flexible tip 24 and squeeze bulb 26 may be secured via collars 44, 46, respectively, to an outer membrane 48 which encloses the shaft 22, e.g., for purposes of protecting the needle 20 against contamination. Advantageously, the collar 46 is rigidly fixed to the hollow shaft 22, while the collar 44 may be easily dislodged in use for reasons which will be apparent below. The outer membrane 48 may be a thin polyethylene or plastic sleeve. Alternatively, the membrane 48 may be an opaque, or combination of opaque and transparent, elastic material such as that used in sewing cloth. In another embodiment, the membrane 48 covers the entire needle 20, including the flexible tip 24. This tends to keep the entire needle 20 in a sterile condition prior to use. Furthermore, a topical agent, such as an antiseptic fluid or paste, may be pre-applied to the flexible tip 24 during manufacture, prior to covering with the membrane 48. The membrane 48 thus prevents evaporation and contamination of the topical agent. The membrane 48 may also have different thicknesses. For instance, the membrane 48 may be thinner over the squeeze bulb so that it is transparent or opaque. This enables determining the volume of the fluid in the squeeze bulb 26.

Figure 3:
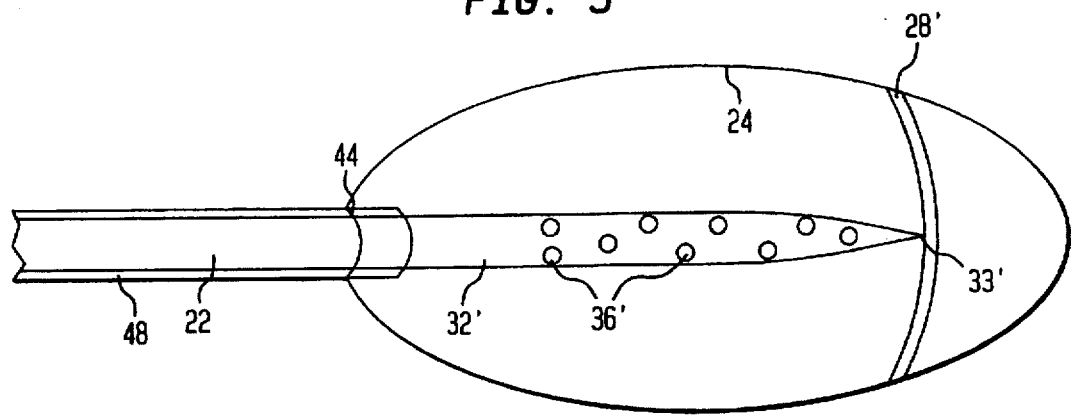
FIG. 3 depicts a needle tip of an injection needle according to an embodiment of the present invention.

Illustratively, the hollow shaft has a sharp needle tip 32. The needle tip 32 illustratively is entirely contained within the flexible tip 24. As shown, the sharp needle tip 32 has a beveled edge with an outlet 36 connected to an axial bore of the hollow shaft 22. For instance, the sharp point 33 may be at the vertex of an angle of approximately 25°. However, the needle tip may be a variety of shapes. For instance, FIG. 3 shows an alternative needle design wherein the needle tip 32' is conical, like a sewing needle, coming to a sharp point 33'. The needle tip 32' is hollow and connected to the hollow shaft 22. Plural outlets 36' are provided which may be laser drilled in a helical pattern, or some other pattern, about the needle tip 32'. The outlets 36' can communicate a fluid from within the hollow shaft 22 to the outside in the vicinity of the needle tip 32'. Note that the indicia 28' may be in the form of a ring provided on the outer surface of the flexible tip 24. The ring indicates the relative location of the sharp point 33', i.e., where it begins. This aids the operator in administering the injection so as to avoid piercing bone with the sharp point 33'.

Opposite the needle tip 32 is a sharp squeeze bulb puncturing tip 34. The sharp puncturing tip 34 illustratively also has a beveled edge (e.g., at an angle of approximately 35°) with an inlet 38 connected to the axial bore of the hollow shaft 22. Opposite the inlet 38 is the outer skin 40 of the squeeze bulb 26. The outer skin illustratively comprises a thin portion/diaphragm or membrane 40 axially disposed in the vicinity of the squeeze bulb puncturing tip 34 with thicker portions 42 surrounding the thin skin portion 40 in an annular fashion. The thicker portions may form longitudinal ribs (extending in parallel to the axis of the hollow shaft 22) that meet at the annulus 42. Illustratively, the thin skin 40 is sufficiently thin to be easily punctured by the squeeze bulb puncturing tip 34 while the thicker skin portions 42 resists puncturing.

Figure 2B:
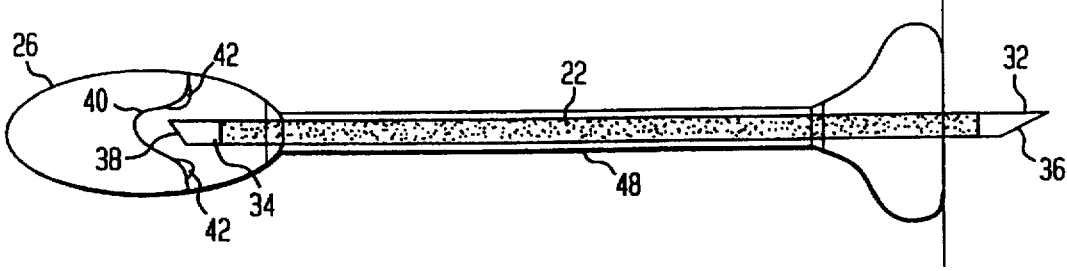
Figure 2C:
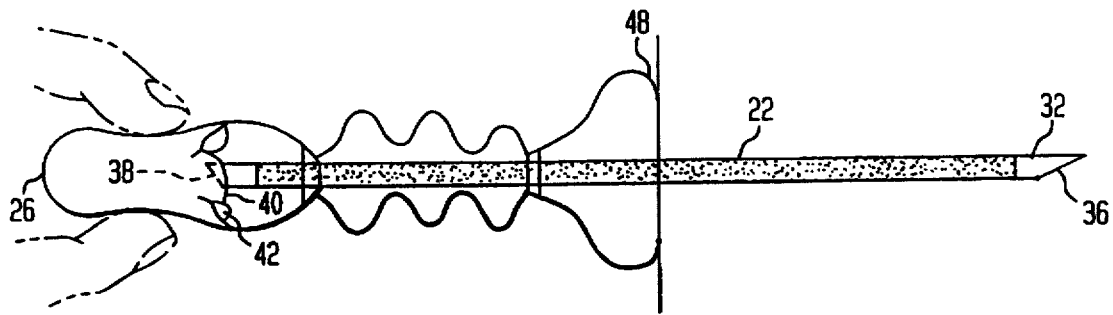

The operation of the camouflaged injection needle 20 is illustrated in FIGS. 2(b)–(c). If necessary, the operator removes the portion of the membrane 48 covering the flexible tip 24. Illustratively, the operator dips the flexible tip 24 into a topical agent such as an antiseptic fluid or paste. Alternatively, the flexible tip 24 may be precoated with the topical agent. The flexible tip 24 absorbs topical agent or the topical agent adheres to the outer surface texture of the flexible tip 24. The operator then brushes the location of the patient's outer human tissue (e.g., epidermis, mucous membrane, etc.) in the vicinity at which the injection is to be administered to clean and disinfect the outer human tissue. The operator then positions the camouflaged injection needle 20 so that the flexible tip 24 is approximately parallel to the direction in which the needle is to be urged, e.g., perpendicular to the surface of the patient's outer human tissue. While grasping the hollow shaft 22 (or finger grip, as described below) with one hand, the operator urges the flexible tip 24 against the patient's outer human tissue. Because the flexible tip 24 is made of a flexible material, the needle tip 32 easily punctures through the flexible tip, contacts the outer surface of the outer human tissue and then punctures through the outer human tissue. With a slight additional pressure needed to push the sharp needle tip 32 through the outer tissue, the collar 44 detaches from is fixed position at the flexible tip end of the shaft for free sliding along the length of the shaft 22. As shown, the outer membrane 48 retracts/accumulates along the squeeze bulb 26 end of the hollow shaft 22. In the case that the outer membrane 48 is an elastic material, the retracting outer membrane does not bunch up in an accordion fashion.

The operator then squeezes the squeeze bulb 26. Because, the squeeze bulb 26 contains fluid, the thin skin portion 40 expands in the direction of the squeeze bulb puncturing tip 34 until the puncturing tip 34 pierces the thin skin 40. The fluid contained in the squeeze bulb 26 is communicated via the inlet 38 of the squeeze bulb puncturing tip 34, through the hollow shaft 22 to the outlet 36 of the needle tip 32 below the outer human tissue. Illustratively, the thin skin 40 forms a fluid tight seal against the hollow shaft 22 near the squeeze bulb puncturing tip 34 so that no fluid escapes.

As noted above, the camouflaged injection needle 20 may deliver a variety of medicinal fluids below the outer human tissue. For instance, the injection needle may deliver an anesthetic fluid to the vicinity of nerve endings. Since such fluids are not delivered directly into blood vessels, any air delivered through the needle prior to injecting the anesthetic fluid does not introduce a health risk to the patient. In the case that the medicinal fluid is to be delivered into a blood vessel, the operator may squeeze the squeeze bulb 26 prior to forcing the needle tip 32 through the flexible ellipsoid end 24 until fluid is communicated through the hollow shaft and out of the outlet 36. This will expel any air present in the hollow shaft 22. Alternatively, the needle 20 may be modified so that the bore of the hollow shaft 22 is pre-filled with the same fluid as in the squeeze bulb 26. The inlet 38 and outlet 36 may be sealed with a membrane to prevent the fluid from escaping (and air being introduced into the hollow shaft 22). When the operator squeezes the squeeze bulb 26, the force of the expelled fluid ruptures both membranes so that fluid is introduced into the blood vessels.

Figure 4:
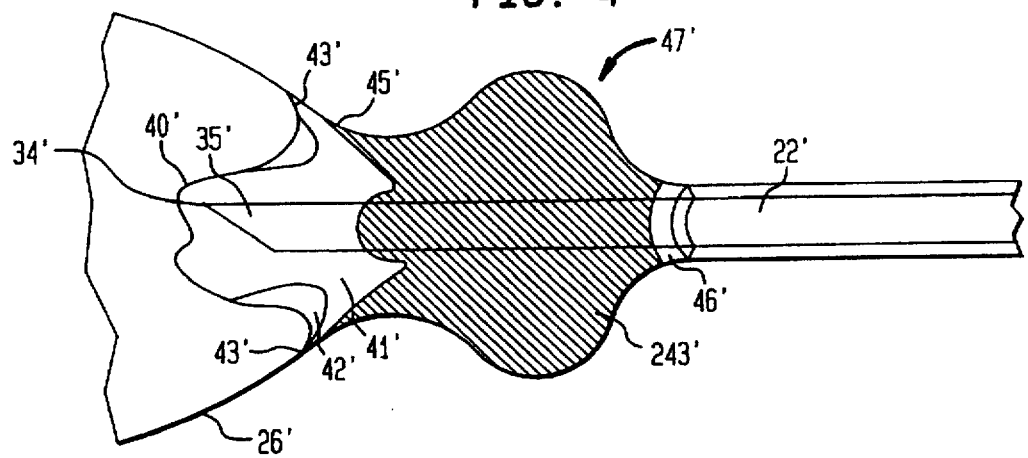
FIG. 4 depicts a bulb with finger grip of an injection needle according to an embodiment of the present invention.

FIG. 4 depicts a modified squeeze bulb 26'. As before, the squeeze bulb 26' contains an injectable fluid in a sealed skin having thick portions 42' and a thin, puncturable portion 40'. As before, the puncturable portion 40' is punctured by the sharp point 35' of the squeeze bulb puncturing tip 34' when the puncturable portion 40' bows outward towards the squeeze bulb puncturing tip 34'. To facilitate the expansion of the thin skin portion 40' of the squeeze bulb 26' (and the squeeze bulb 26 of FIGS. 2(a)–(c)), a vented air space 41' is provided. Note that the annular thick portion 42' can be connected to the rest of the squeeze bulb 26 by a thin portion 43'. Under manual pressure, the thin portion 43' stretches so that both the thick annular portion 42' and the thin skin portion 40' move in the direction of the sharp puncturing tip 35'.

As shown, a solid annular bulbous portion 243' is connected to the hollow shaft 22' forward of the squeeze bulb 26' and puncturing tip 35'. The bulbous portion 243' may be made of the same material as the squeeze bulb 26 or may be made of a harder material. The bulbous portion 243' illustratively may be bonded to the hollow shaft 22' at the collar 46' by a variety of methods such as crimping, cementing, etc. The overall shape of the cross-section of the squeeze bulb 26' and bulbous portion 243' is roughly hour-glass shaped. The minimum diameter portion of the outer surface 45' of the bulbous portion 243' and 26' form a finger grip 47' for urging the needle tip, e.g., the needle tip 32, through the flexible tip 24 and outer human tissue.

Figure 5A:
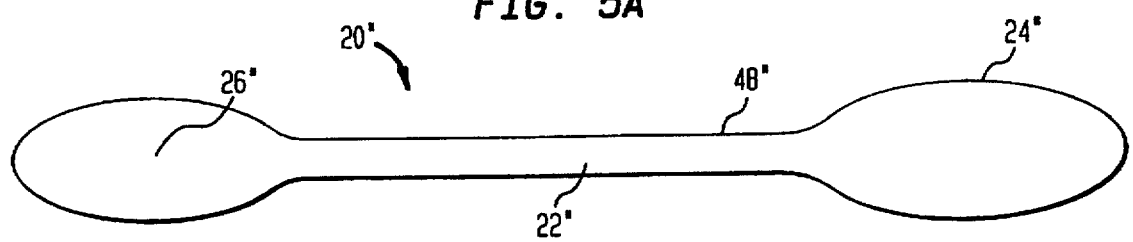
FIGS. 5(a)–(c) depict a blunt dissection injection needle according to an embodiment of the present invention.
Figure 5B:
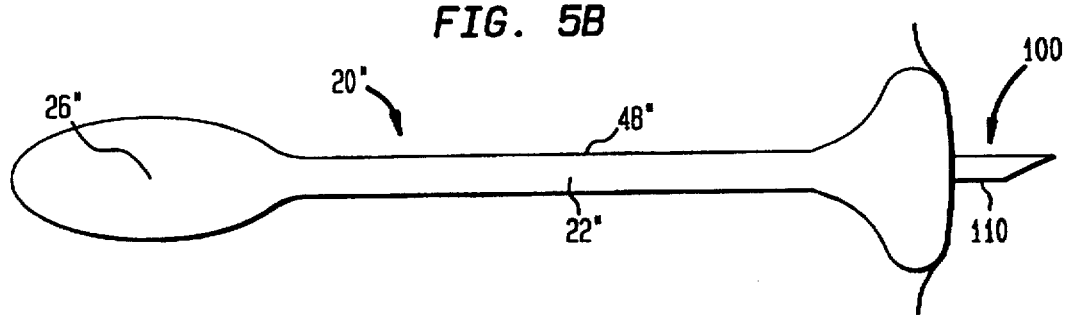
Figure 5C:
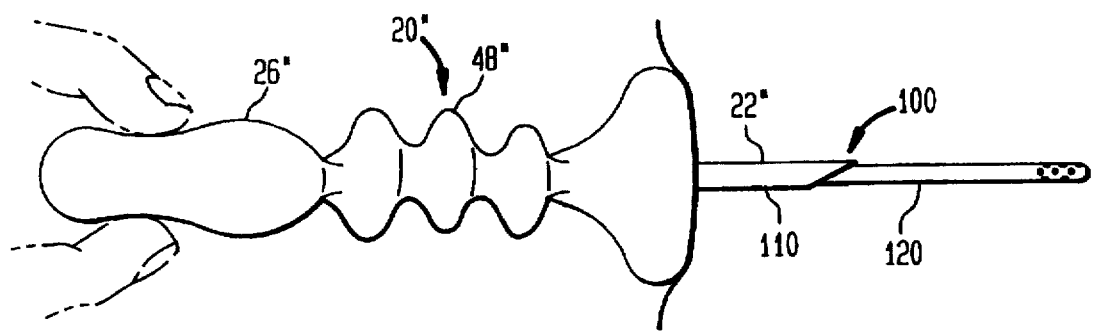

FIGS. 5(a)–(c) depict a camouflaged injection needle 20" according to yet another embodiment. As before, the camouflaged injection needle 20" has a hollow shaft 22", a flexible ellipsoid tip 24" and a squeeze bulb 26". Both the flexible tip 24" and squeeze bulb 26" appear continuous with a membrane 48" which conceals the shaft 22". Within the flexible ellipsoid tip 24" is a needle tip 100. As shown, the needle tip 100 includes a sharp outer needle tip 110 for piercing upper human tissues and a blunt inner needle tip 120 for bluntly dissecting lower layer tissues. Illustratively, the needle tips 110 and 120 may be formed from any suitable needle tip material such as metal or plastic.

Figure 6:
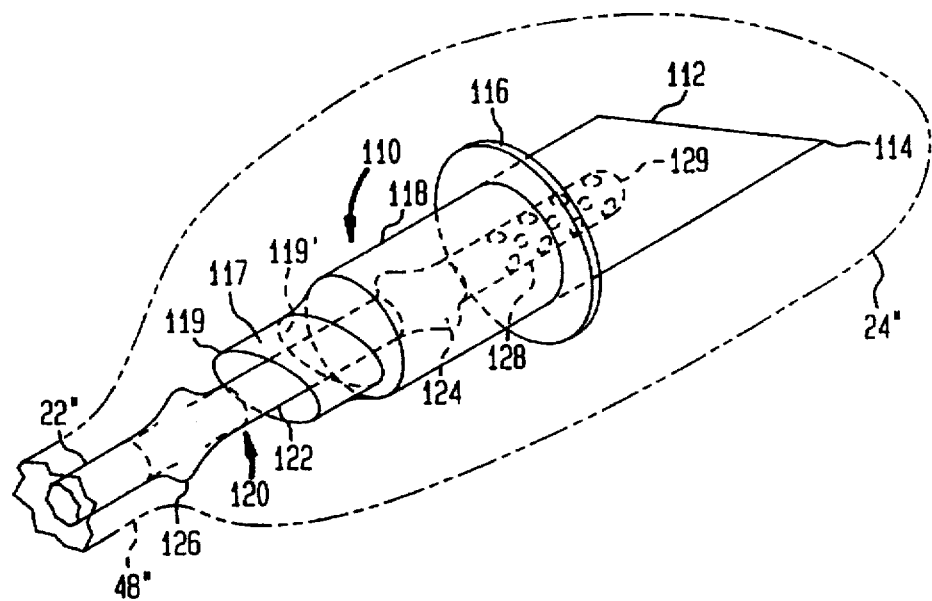
FIG. 6 depicts a needle tip of the blunt dissection injection needle of FIGS. 5(a)–(c) in greater detail.

FIG. 6 depicts a needle tip 100 design for the camouflaged injection needle 20" in greater detail. As shown, the needle tip 100 includes a sharp outer needle tip 110 and a blunt inner needle tip 120 positioned therein and axially aligned therewith. The blunt inner needle 120 is connected at one end to the hollow shaft and has holes 128 for delivering fluid from the hollow shaft. The blunt inner needle tip 120 illustratively has an outer diameter in the range of 5 gauge to 30 gauge and has a rounded end 129. As shown, the blunt inner needle 120 has a shaft 122 with widened flanges 124 and 126 positioned thereon. The shaft 122 is connected and integral with the shaft 22". Illustratively, the shaft 122–22" is 6"–8" in length. The flanges 124 and 126 may be formed at the distances of about 0.5" and 0.75", respectively, from the penetrating rounded end 129 of the blunt inner needle 120. These flanges 124, 126 may be formed by simply crimping the blunt inner needle shaft 122. The flanges 124 and 126 are mutually perpendicular and extend perpendicularly to the axis of the shaft 122 (the flanges 124, 126 and axis of the shaft 122 are orthogonal). Furthermore, one flange 124 is located within the shaft 118 of the sharp outer needle 110, while the other flange 126 is located outside of the shaft 118 of the sharp outer needle 110. The shaft of the sharp outer needle 110 has an elliptical end 117 positioned between the two flanges 124 and 126. As shown, the flange 126, when urged towards the sharp outer needle 110, meets the lip 119 of the elliptical end 117. As a result, if the blunt inner needle 120 is not rotated with respect to the sharp outer needle 110, then the blunt inner needle 120 will remain within the sharp outer needle 110 even if the blunt inner needle 120 is urged in the direction of the sharp outer needle 110. This enables the operator to cause the sharp outer needle 110 to pierce through the flexible tip 24" and into the outer human tissue without dislodging the blunt inner needle 120. Likewise, if the hollow shaft 22" is rotated and then urged in the opposite direction, the flanges 124 meet the inner lip 119' and cannot pass through. Note that indicia may be provided on the outer surface of the flexible tip 24 which indicate the orientation and location of the sharp point 114. This aids the operator in avoiding puncturing bone with the sharp point 114.

The sharp outer needle 110 includes a beveled edge 112 that forms a sharp point 114, with a vertex of about 25°, capable of piercing both the flexible tip 24" and the outer human tissue surface. The sharp outer needle 110 has a shaft which may be about 0.3"–1" in length overall. On the shaft 118 of the sharp outer needle tip 110 is a penetration limiting ring 116. The penetration limiting ring 116 may have an outer diameter of about 0.15" and may be formed at a distance of about 0.25" from the sharp point 114. Illustratively, when the hollow shaft 22" is urged in the direction of the flexible tip 24", the sharp outer needle tip 110 penetrates through the flexible tip 24". However, the material of the flexible tip 24" retracts/accumulates on the penetration limiting ring 116 which does not easily pass through the flexible tip 24". Furthermore, the penetration limiting ring 116 does not pass through the outer human tissues surface, but rather rests thereon. This limits the penetration depth of the sharp outer needle 110 so that damage to tissues below the outer human tissue is reduced.

The operation of the camouflaged injection needle 20" is illustrated in FIGS. 5(a)–(c). The operation is similar to that described above except as follows. The operator urges the hollow shaft 22" so that the flexible tip 24" pushes against the outer human tissue. Illustratively, this is done without rotating the hollow shaft 22". Thus, the flange 126 engages the lip 119 of the flattened portion 117 of the shaft 118 of the sharp outer needle 110. As such, the axial force on the hollow shaft 22" is transmitted to the sharp outer needle 110 which is urged towards the outer human tissues and pierces through the flexible tip 24" and the outer human tissue. In so doing, excess material from the flexible tip 24" retracts along the shaft 118 of the sharp outer needle 110 and accumulates on the penetration limiting ring 116.

The operator urges the shaft 22" until the penetration limiting ring 116 (or excess flexible material thereon) meets the outer human tissue surface. The operator then rotates the hollow shaft 90°. This aligns the flange 126 with the major axis of the elliptical portion 117 of the shaft 118 of the outer needle 110 so that the flange 126 may pass through the elliptical portion 117. The operator then again urges the hollow shaft 22" towards the outer human tissue. Because the flange 126 does not meet the lip 119 of the elliptical shaft portion 117 but rather passes through into the sharp outer needle 110, the blunt inner needle tip 120 penetrates more deeply into the patient below the outer human tissues. Illustratively, the blunt inner needle tip 120 penetrates by bluntly dissecting the tissues rather than piercing through them. Thus, damage to the lower level tissues is reduced.

The operator extends the blunt inner needle tip 120 to the desired depth and then squeezes the squeeze bulb 26" to deliver the fluid thereat. Then, without rotating the hollow shaft, the operator withdraws the shaft 22". First, only the blunt inner needle tip 120 retracts from within the patient. Eventually, as the blunt inner needle tip 120 retracts, the flange 124 meets the lip 119' of the elliptical portion of the shaft 118 and does not pass therethrough. As the operator continues to withdraw the hollow shaft 22", the sharp outer needle 110 is withdrawn from the patient.

Figure 1:
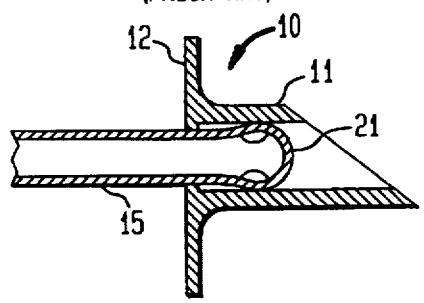
FIG. 1 depicts a prior art injection needle.
Figure 7:
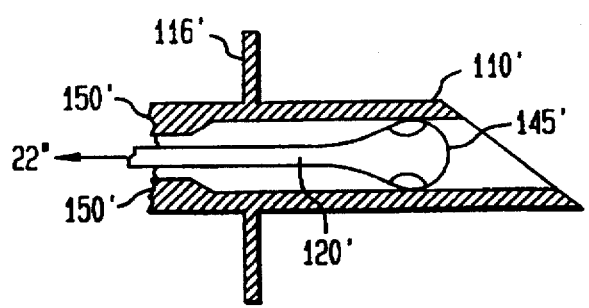
FIG. 7 depicts another needle tip of the blunt dissection injection needle of FIGS. 5(a)–(c) in greater detail.

As shown in FIG. 7 the needle tip 100 may also be constructed similar as depicted in FIG. 1. That is, the inner blunt needle 120' may be formed with a bulbous end 145' that engages the inner sides of the bore of the outer needle 110' by a friction fit. Such a bulbous end 145' may be formed by adding a drop of an appropriate chemically unreactive solder, such as platinum, gold or stainless steel to the end of the inner needle tip 120'. Alternatively, an inert plastic or acrylic material may be bonded to the end 145' of the inner needle tip 120'. Alternatively, the bulbous shaped end 145' may be formed while forming the rest of the inner needle tip 120', i.e., as part of the molding process.

In any event, as described above, the injection can be delivered by urging the needle tip 100 forward. Initially, the friction fit of the bulbous needle end 145' within the outer needle tip 110' causes the inner needle tip 120' to remain within the outer needle tip 110'. The outer needle tip 110' pierces through the flexible tip 24" and outer human tissues until a flange 116' meets the surface of the outer tissue. Continued pressure dislodges the blunt inner needle 120' for deeper penetration. The operator then squeezes the squeeze bulb 26" to deliver the injection. The hollow shaft 22" is then withdrawn. First, this causes only the inner needle tip 120' to withdraw. The sharp outer needle 110' may also have a narrowed neck 150' of its inner diameter recessed somewhat within its bore. As the inner needle 110' withdraws, the bulbous end 145' catches the narrowed neck 150'. Further withdrawal of the shaft 22" transmits a force via the bulbous end 145' and neck 150' which withdraws the sharp outer needle 120' from the patient.

In short, a camouflaged injection needle is disclosed including a shaft, a flexible ellipsoid tip at one end of the shaft and a sharp needle tip positioned within the flexible tip and axially aligned with the shaft. The sharp needle tip is capable of piercing through the flexible tip and into an outer human tissue when the flexible tip is positioned on the outer human tissue and the shaft is urged in the direction of the outer human tissue. The injection needle is camouflaged to resemble a cotton swab. This reduces pre-injection anxiety of the patient.

Finally, the above discussion is intended to be merely illustrative. Numerous alternative embodiments may be devised by those having ordinary skill in the art without departing from the spirit and scope of the following claims.

The claimed invention is:

1. A camouflaged injection needle comprising:
   a hollow shaft that communicates a fluid therethrough in an axial direction from a distal end to a proximal end of said shaft,
   a needle tip extending from said proximal end of, and axially aligned with, said hollow shaft, and
   a flexible ellipsoid tip connected to only said proximal end of said shaft which entirely contains and conceals said needle tip and which exposes said distal end to said shaft,
   said flexible ellipsoid tip comprising a polymer with a plurality of pockets distributed therein so as to facilitate said needle tip puncturing through said flexible ellipsoid tip and into outer human tissue when said flexible ellipsoid tip is positioned adjacent to the outer human tissue and said shaft is manually urged axially towards the outer human tissue.

2. The injection needle of claim 1 further comprising:
   a squeeze bulb containing a fluid therein, attached to a second end of said shaft opposite said needle tip, said squeeze bulb communicating a fluid contained therein through said shaft towards said needle tip, in response to manually squeezing said squeeze bulb, for delivering said fluid below the outer human tissue.

3. The injection needle of claim 2 wherein said squeeze bulb resembles a swab tip of a cotton swab.

4. The injection needle of claim 3 wherein said squeeze bulb comprises a finger grip positioned on an outer diameter of said hollow shaft.

5. The injection needle of claim 2 wherein said hollow shaft comprises a puncturing tip on said second end pointing in a direction of said squeeze bulb and wherein said squeeze bulb comprises a portion which expands in a direction of, and is punctured by said puncturing tip in response to manually squeezing said squeeze bulb.

6. The injection needle of claim 1 further comprising:
   a blunt dissection needle tip connected to said hollow shaft, having a smaller diameter than, and axially positioned within, said needle tip, said blunt dissection needle being extendible from said needle tip, after said needle tip punctures the outer human tissue, for bluntly dissecting tissues below the outer human tissue.

7. The injection needle of claim 6
   wherein said needle tip comprises a sharp point for piercing through said flexible tip and the outer human tissue, an elliptical end with a lip opposite said sharp point and a penetration limiting ring positioned on an outer surface of said needle tip between said sharp point and said elliptical end,
   wherein said hollow shaft comprises a flange which meets said lip and transmits an axial force of said shaft to cause said sharp point to pierce through said flexible tip and the outer human tissue until said penetration limiting ring limits further penetration,
   said hollow shaft also being rotatable so that said flange passes through said elliptical end so as to extend said blunt dissection needle tip from said needle tip deeper into lower layer tissues.

8. The injection needle of claim 1 wherein said flexible ellipsoid tip resembles a swab tip of a cotton swab, and wherein said hollow shaft resembles a cotton swab shaft, so that said injection needle resembles a cotton swab.

9. The injection needle of claim 1 wherein said flexible ellipsoid tip is sufficiently absorbent to absorb, and to apply, topical agents to the outer human tissue prior to puncturing said outer human tissue with the needle tip.

10. The injection needle of claim 1 wherein said flexible ellipsoid tip has an outer surface texture to which topical agents adhere, said surface texture adhering to a sufficient amount of one of said topical agents to apply said one topical agent to the outer human tissue prior to puncturing the outer human tissue with said needle tip.

11. A camouflaged injection needle comprising:
   a hollow shaft configured to communicate a fluid therethrough in an axial direction from a distal end to a proximal end of said shaft, a needle tip extending from said proximal end of, and axially aligned with, said hollow shaft, a flexible ellipsoid tip connected to said proximal end of said hollow shaft, which contains said needle tip, said flexible ellipsoid tip being sufficiently flexible to enable said needle tip to puncture through said flexible ellipsoid tip and into outer human tissue when said flexible ellipsoid tip is positioned adjacent to the human tissue and said shaft is manually urged axially towards the human tissue, and a blunt dissection needle tip connected to said hollow shaft, having a smaller diameter than, and axially positioned within, said needle tip, said blunt dissection needle tip being extendible from said needle tip, after said needle tip punctures the outer human tissue, for bluntly dissecting tissues below the outer human tissue.

12. The camouflaged injection needle of claim 11:

wherein said needle tip comprises a tube that is axially aligned with said shaft, said tube comprising a sharp point for piercing through said flexible tip and the outer human tissue, and a flattened circumferential lip opposite said sharp point, said needle tip also comprising a penetration limiting ring positioned on an outer surface of said needle tip between said sharp point and said lip, wherein said hollow shaft comprises a flange positioned on its outer surface to meet said lip and transmit an axial force of said shaft to cause said sharp point to pierce through said flexible tip and the outer human tissue until said penetration limiting ring limits further penetration, and wherein said hollow shaft is rotatable so that said flange passes through said lip so as to extend said blunt dissection needle tip from said needle tip deeper into lower layer tissues.

13. A camouflaged injection needle comprising:

a hollow shaft configured to communicate a fluid therethrough in an axial direction from a distal end to a proximal end of said shaft, a squeeze bulb containing a fluid therein, attached to said distal end of said shaft, a puncturing tip positioned at said distal end of said shaft and pointing in a direction of said squeeze bulb, wherein said squeeze bulb comprises a portion which expands in a direction of, and is punctured by, said puncturing tip, in response to manually squeezing said squeeze bulb, a needle tip extending from said proximal end of, and axially aligned with, said hollow shaft, and a flexible ellipsoid tip connected to said proximal end of said hollow shaft, which contains said needle tip.

14. A method for administering an injection comprising:

positioning a flexible tip, that comprises a polymer with a plurality of pockets distributed therein, of a concealed injection needle over an outer human tissue below which an injection is to be delivered, said flexible tip being connected to only a proximal end of a hollow shaft of said concealed injection needle which entirely contains and conceals a sharp needle tip of said concealed injection needle and which exposes a distal end of said hollow shaft, urging said hollow shaft of said injection needle towards the outer human tissue, and piercing said sharp needle tip, that is concealed within said flexible tip and axially aligned with said urged shaft, through said flexible tip and into the outer human tissue, wherein said polymer with said plurality of pockets facilitates said ability of said sharp needle to pierce through said flexible tip.

15. The method of claim 14 further comprising the step of:

squeezing a squeeze bulb of said injection needle to communicate a fluid therein through said hollow shaft and out of said injection needle below the outer human tissue.

16. The method of claim 15 further comprising the step of:

piercing a portion of said squeeze bulb with a piercing tip of said hollow shaft opposite said needle tip.

17. The method of claim 14 further comprising the step of:

extending a blunt dissection needle from within said needle tip into lower layer tissues.

18. The method of claim 17 further comprising after said step of piercing but before said step of extending, the step of:

aligning a flange on an outer surface of said hollow shaft so as to pass through a flattened end of said needle tip by rotating said hollow shaft.

19. The method of claim 14 further comprising, before said step of positioning, the step of:

concealing an injection needle as a cotton swab.

20. A method for administering an injection comprising:

positioning a flexible tip of a concealed injection needle over an outer human tissue below which an injection is to be delivered, urging a hollow shaft of said injection needle towards the outer human tissue, piercing a sharp needle tip, that is concealed within said flexible tip and axially aligned with said urged shaft, through said flexible tip and into the outer human tissue, and extending a blunt dissection needle from within said needle tip into lower layer tissues.

21. The method of claim 20 further comprising:

after said step of piercing, but before said step of extending, aligning a flange on an outer surface of said hollow shaft so as to pass through a flattened end of said needle tip by rotating said hollow shaft.

22. A method for administering an injection comprising:

positioning a flexible tip of a concealed injection needle over an outer human tissue below which an injection is to be delivered, urging a hollow shaft of said injection needle towards the outer human tissue, piercing a sharp needle tip, that is concealed within said flexible tip, and axially aligned with said urged hollow shaft, through said flexible tip and into the outer human tissue, squeezing a squeeze bulb of said injection needle to communicate a fluid therein through said hollow shaft and out of said injection needle below the outer human tissue, and piercing a portion of said squeeze bulb with a piercing tip of said hollow shaft opposite said needle tip.

* * * * *